US012632502B2

(12) United States Patent
    Agassi et al.

(10) Patent No.: US 12,632,502 B2
(45) Date of Patent: May 19, 2026

(54) SYSTEMS AND METHODS FOR ONTOLOGICALLY CLASSIFYING RECORDS

(71) Applicant: Cerner Innovation, Inc., Kansas City, MO (US)

(72) Inventors: Natalee Agassi, Blue Bell, PA (US); William John Ormerod, Jr., Fairfax, VT (US); Todd Wyeth Fritsche, Phoenixville, PA (US)

(73) Assignee: Cerner Innovation, Inc., Kansas City, MO (US)

( * ) Notice: Subject to any disclaimer, the term of this patent is extended or adjusted under 35 U.S.C. 154(b) by 0 days.

(21) Appl. No.: 18/771,008

(22) Filed: Jul. 12, 2024

(65) Prior Publication Data

US 2024/0362274 A1 Oct. 31, 2024

Related U.S. Application Data

(63) Continuation of application No. 17/736,964, filed on May 4, 2022, now Pat. No. 12,072,941.

(51) Int. Cl.
G06F 16/906 (2019.01)
G16H 10/60 (2018.01)

(52) U.S. Cl.
CPC ........... G06F 16/906 (2019.01); G16H 10/60 (2018.01)

(58) Field of Classification Search
CPC ..... G06F 16/906; G06F 16/367; G16H 10/60; G16H 70/00
See application file for complete search history.

(56) References Cited

U.S. PATENT DOCUMENTS

| | | | |
|---|---|---|---|
| 4,502,708 A | 3/1985 | Taplin |
| 4,847,764 A | 7/1989 | Halvorson |
| 5,072,383 A | 12/1991 | Brimm et al. |
| 5,077,666 A | 12/1991 | Brimm et al. |
| 5,530,861 A | 6/1996 | Diamant et al. |

(Continued)

FOREIGN PATENT DOCUMENTS

| | | |
|---|---|---|
| CN | 101639837 A | 2/2010 |
| CN | 114026651 A | 2/2022 |

(Continued)

OTHER PUBLICATIONS

Amador-Dominguez, An ontology-based deep learning approach for triple, classification with out-of-knowledge-base entities, pp. 85-102, (Feb. 19, 2021).*

(Continued)

*Primary Examiner* — Albert M Phillips, III
(74) *Attorney, Agent, or Firm* — Invoke

(57) ABSTRACT

Systems and methods are described for procedurally-based decision support using ontology-based classification of database records. The procedural decision support can facilitate extraction of contextually relevant data from a database. The data may be formatted for compatibility with a knowledge-based data library using one or more scripts and populated in the library as an entity. Classification of the entity can be reasoned using the available data. One or more classifications of the entity may be returned to the procedural decision support to facilitate computation of a recommendation.

20 Claims, 6 Drawing Sheets

(56)　　　　References Cited

U.S. PATENT DOCUMENTS

| | | | |
|---|---|---|---|
| 5,692,125 A | 11/1997 | Schloss et al. |
| 5,721,913 A | 2/1998 | Ackroff et al. |
| 5,745,901 A | 4/1998 | Entner et al. |
| 5,758,095 A | 5/1998 | Albaum et al. |
| 5,784,635 A | 7/1998 | McCallum |
| 5,790,119 A | 8/1998 | Sklut et al. |
| 5,799,297 A | 8/1998 | Goodridge et al. |
| 5,826,239 A | 10/1998 | Du et al. |
| 5,832,455 A | 11/1998 | Hayashi et al. |
| 5,842,173 A | 11/1998 | Strum et al. |
| 5,842,976 A | 12/1998 | Williamson |
| 5,911,687 A | 6/1999 | Sato et al. |
| 5,923,018 A | 7/1999 | Kameda et al. |
| 5,937,388 A | 8/1999 | Davis et al. |
| 5,970,463 A | 10/1999 | Cave et al. |
| 5,987,422 A | 11/1999 | Buzsaki |
| 5,991,728 A | 11/1999 | Debusk et al. |
| 6,014,629 A | 1/2000 | Debruin-Ashton |
| 6,037,940 A | 3/2000 | Schroeder et al. |
| 6,052,669 A | 4/2000 | Smith et al. |
| 6,052,684 A | 4/2000 | Du |
| 6,061,506 A | 5/2000 | Wollaston et al. |
| 6,064,984 A | 5/2000 | Ferguson et al. |
| 6,067,548 A | 5/2000 | Cheng |
| 6,072,493 A | 6/2000 | Driskell et al. |
| 6,078,982 A | 6/2000 | Du et al. |
| 6,085,184 A | 7/2000 | Bertrand et al. |
| 6,088,679 A | 7/2000 | Barkley |
| 6,115,646 A | 9/2000 | Fiszman et al. |
| 6,151,583 A | 11/2000 | Ohmura et al. |
| 6,208,345 B1 | 3/2001 | Sheard et al. |
| 6,208,974 B1 | 3/2001 | Campbell et al. |
| 6,223,164 B1 | 4/2001 | Seare et al. |
| 6,225,998 B1 | 5/2001 | Okita et al. |
| 6,278,901 B1 | 8/2001 | Winner et al. |
| 6,279,009 B1 | 8/2001 | Smirnov et al. |
| 6,304,886 B1 | 10/2001 | Bernardo et al. |
| 6,308,163 B1 | 10/2001 | Du et al. |
| 6,308,188 B1 | 10/2001 | Bernardo et al. |
| 6,311,192 B1 | 10/2001 | Rosenthal et al. |
| 6,314,556 B1 | 11/2001 | Debusk et al. |
| 6,347,329 B1 | 2/2002 | Evans |
| 6,349,329 B1 | 2/2002 | Mackintosh et al. |
| 6,430,538 B1 | 8/2002 | Bacon et al. |
| 6,458,080 B1 | 10/2002 | Brown et al. |
| 6,484,144 B2 | 11/2002 | Martin et al. |
| 6,578,006 B1 | 6/2003 | Saito et al. |
| 6,697,784 B2 | 2/2004 | Bacon et al. |
| 6,728,947 B1 | 4/2004 | Bengston |
| 6,912,549 B2 | 6/2005 | Rotter et al. |
| 6,915,265 B1 | 7/2005 | Johnson |
| 6,966,049 B2 | 11/2005 | Lepejian et al. |
| 6,970,844 B1 | 11/2005 | Bierenbaum |
| 6,978,268 B2 | 12/2005 | Thomas et al. |
| 7,027,997 B1 | 4/2006 | Robinson et al. |
| 7,035,862 B2 | 4/2006 | Patitucci |
| 7,047,535 B2 | 5/2006 | Lee et al. |
| 7,051,012 B2 | 5/2006 | Cole et al. |
| 7,136,824 B2 | 11/2006 | Masuda et al. |
| 7,181,375 B2 | 2/2007 | Rao et al. |
| 7,184,967 B1 | 2/2007 | Mital et al. |
| 7,240,324 B2 | 7/2007 | Casati et al. |
| 7,275,039 B2 | 9/2007 | Setteducati |
| 7,296,056 B2 | 11/2007 | Yaung |
| 7,318,059 B2 | 1/2008 | Thomas et al. |
| 7,403,936 B2 | 7/2008 | Giang et al. |
| 7,428,495 B2 | 9/2008 | Dhar et al. |
| 7,437,302 B2 | 10/2008 | Haskell et al. |
| 7,447,644 B2 | 11/2008 | Brandt et al. |
| 7,457,731 B2 | 11/2008 | Rao |
| 7,457,765 B2 | 11/2008 | Thompson et al. |
| 7,590,932 B2 | 9/2009 | Britton et al. |
| 7,617,078 B2 | 11/2009 | Rao et al. |
| 7,630,947 B2 | 12/2009 | Pandya et al. |
| 7,653,566 B2 | 1/2010 | Kim et al. |

| | | | |
|---|---|---|---|
| 7,689,441 B1 | 3/2010 | Craft |
| 7,711,404 B2 | 5/2010 | Rao et al. |
| 7,725,330 B2 | 5/2010 | Rao et al. |
| 7,744,540 B2 | 6/2010 | Rao et al. |
| 7,756,728 B2 | 7/2010 | Maughan et al. |
| 7,805,385 B2 | 9/2010 | Steck et al. |
| 7,840,511 B2 | 11/2010 | Rosales et al. |
| 7,844,560 B2 | 11/2010 | Krishnan et al. |
| 7,877,272 B2 | 1/2011 | Rosales et al. |
| 7,890,349 B2 | 2/2011 | Cole et al. |
| 7,895,055 B2 | 2/2011 | Schneider et al. |
| 7,917,377 B2 | 3/2011 | Rao et al. |
| 7,937,655 B2 | 5/2011 | Teng et al. |
| 8,000,978 B2 | 8/2011 | Wager et al. |
| 8,027,849 B2 | 9/2011 | Johnson et al. |
| 8,046,362 B2 | 10/2011 | Bayliss |
| 8,200,527 B1 | 6/2012 | Thompson et al. |
| 8,214,224 B2 | 7/2012 | Rao et al. |
| 8,214,225 B2 | 7/2012 | Rao et al. |
| 8,219,416 B2 | 7/2012 | Auker et al. |
| 8,280,750 B2 | 10/2012 | Krishnan et al. |
| 8,326,667 B2 | 12/2012 | Johnson |
| 8,392,152 B2 | 3/2013 | Rao |
| 8,392,232 B2 | 3/2013 | Mcgillin |
| 8,571,884 B2 | 10/2013 | Badgett et al. |
| 8,579,784 B2 | 11/2013 | Krishnan et al. |
| 8,694,518 B2 | 4/2014 | Schultz et al. |
| 8,768,741 B1 | 7/2014 | Hinton et al. |
| 8,775,207 B2 | 7/2014 | Abraham et al. |
| 9,336,283 B2 | 5/2016 | Giang et al. |
| 9,639,662 B2 | 5/2017 | Sethumadhavan et al. |
| 9,703,927 B2 | 7/2017 | Chaudhri et al. |
| 9,824,316 B2 | 11/2017 | Junker et al. |
| 10,628,553 B1 * | 4/2020 | Murrish ............... G16H 70/00 |
| 2001/0001144 A1 | 5/2001 | Kapp |
| 2001/0032108 A1 | 10/2001 | Sieron et al. |
| 2001/0037227 A1 | 11/2001 | McInnis et al. |
| 2002/0018066 A1 | 2/2002 | Amos |
| 2002/0059201 A1 | 5/2002 | Work |
| 2002/0059251 A1 | 5/2002 | Stern et al. |
| 2002/0065701 A1 | 5/2002 | Kim et al. |
| 2002/0128871 A1 | 9/2002 | Adamson et al. |
| 2002/0128890 A1 | 9/2002 | Dick et al. |
| 2002/0129031 A1 | 9/2002 | Lau et al. |
| 2002/0170035 A1 | 11/2002 | Casati et al. |
| 2003/0023593 A1 | 1/2003 | Schmidt |
| 2003/0023728 A1 | 1/2003 | Yaung |
| 2003/0045958 A1 | 3/2003 | Brandt et al. |
| 2003/0050800 A1 | 3/2003 | Brandt et al. |
| 2003/0074225 A1 | 4/2003 | Borsand et al. |
| 2003/0078813 A1 | 4/2003 | Haskell et al. |
| 2003/0078911 A1 | 4/2003 | Haskell et al. |
| 2003/0149714 A1 | 8/2003 | Casati et al. |
| 2003/0158832 A1 | 8/2003 | Sijacic et al. |
| 2004/0015841 A1 | 1/2004 | Lepejian et al. |
| 2005/0027566 A1 | 2/2005 | Haskell |
| 2006/0184475 A1 | 8/2006 | Krishnan et al. |
| 2006/0184943 A1 | 8/2006 | Delmonego et al. |
| 2007/0027738 A1 | 2/2007 | Masuda et al. |
| 2007/0130206 A1 | 6/2007 | Zhou et al. |
| 2008/0140694 A1 | 6/2008 | Mangla |
| 2008/0313204 A1 | 12/2008 | Schultz et al. |
| 2009/0043634 A1 | 2/2009 | Tisdale |
| 2009/0066992 A1 * | 3/2009 | Shepherd ............... G06Q 10/06 |
| | | | 358/1.15 |
| 2009/0089092 A1 | 4/2009 | Johnson et al. |
| 2010/0004948 A1 | 1/2010 | Toomey et al. |
| 2010/0131289 A1 | 5/2010 | Brandt et al. |
| 2011/0071850 A1 | 3/2011 | Nuthi |
| 2011/0320187 A1 | 12/2011 | Motik et al. |
| 2012/0041910 A1 | 2/2012 | Ludik et al. |
| 2012/0239671 A1 | 9/2012 | Chaudhri et al. |
| 2012/0245948 A1 | 9/2012 | Nolte et al. |
| 2012/0253836 A1 | 10/2012 | Nolte et al. |
| 2013/0046558 A1 | 2/2013 | Landi et al. |
| 2013/0085977 A1 | 4/2013 | Junker |
| 2013/0204830 A1 | 8/2013 | Franke |
| 2014/0058748 A1 | 2/2014 | Ford et al. |
| 2014/0095203 A1 | 4/2014 | Anand et al. |

(56) References Cited

U.S. PATENT DOCUMENTS

| | | | |
|---|---|---|---|
| 2014/0244300 A1 | 8/2014 | Bess et al. |
| 2015/0081326 A1 | 3/2015 | Krishnapuram et al. |
| 2015/0120327 A1 | 4/2015 | Compton et al. |
| 2015/0149362 A1 | 5/2015 | Baum et al. |
| 2015/0317311 A1 | 11/2015 | Cannon et al. |
| 2016/0350361 A1 | 12/2016 | Chen et al. |
| 2017/0091388 A1 | 3/2017 | Zolla et al. |
| 2017/0109477 A1 | 4/2017 | Farooq et al. |
| 2017/0124269 A1 | 5/2017 | Mcnair et al. |
| 2017/0161439 A1 | 6/2017 | Raduchel et al. |
| 2017/0212748 A1 | 7/2017 | Agnew et al. |
| 2018/0181644 A1 | 6/2018 | Lyons et al. |
| 2019/0197421 A1 | 6/2019 | Agassi et al. |
| 2019/0197428 A1 | 6/2019 | Kodish-Wachs et al. |
| 2019/0303371 A1 | 10/2019 | Rowe et al. |
| 2020/0342991 A1 | 10/2020 | Hu et al. |
| 2021/0182306 A1 | 6/2021 | Agassi et al. |
| 2022/0044812 A1 | 2/2022 | Barnes et al. |

FOREIGN PATENT DOCUMENTS

| | | | |
|---|---|---|---|
| EP | 0090971 A1 | 10/1983 |
| EP | 0950971 A2 | 10/1999 |
| EP | 1065618 A2 | 1/2001 |
| EP | 1304645 A2 | 4/2003 |
| JP | 2001-202408 A | 7/2001 |
| WO | 99/24927 A1 | 5/1999 |
| WO | 00/03344 A1 | 1/2000 |
| WO | 00/14618 A2 | 3/2000 |
| WO | 00/33238 A2 | 6/2000 |
| WO | 2017/188987 A2 | 11/2017 |

OTHER PUBLICATIONS

Anonymous, "Database," Wikipedia, retrieved from https://en.wikipedia.org/w/index.php?title=Database&oldid=757392515, Dec. 30, 2016, pp. 22.

Anonymous, "Snomed CT," Wikipedia, retrieved from https://en.wikipedia.org/w/index.php?title=SNOMED_CT&oldid=612767614, retrieved on Mar. 15, 2021, pp. 10.

Apelon Products, Retrieved from internet URL: http://apelon.com/products/products . . . authoring.htm, May 22, 2002, 45 pages.

Batch, Kim, "Who Needs a Standard Medical Terminology.", Kim Balch Enterprise Architect Center for Biomedical Information,University of Pittsburgh., 9 pages.

Bechhofer et al., "Terminologies and terminology servers for information environments", Sollware Technology and Engineering Practice, 1997. Proceedings., Eighth IEEE International Workshop on [incorporating Computer Aided Software Engineering]. IEEE, 1997, Jul. 14, 1997, pp. 484-497.

Bertino et al., "A Flexible Model Supporting the Specification and Enforcement of Role-Based Authorization in Workflow Management Systems.", Proceedings of the second ACM workshop on Role-based access, 1997, 12 pages.

Chun et al., "Dynamic Composition of Workflows for Customized eGovernment Service Delivery", Proceedings of the 2002 Annual National Conference on Digital Government Research, May 2002, pp. 1-7.

Dewan et al., "Workflow Optimization Through Task Redesign in Business Information Processes", Proceedings of the Thirty-First Hawaii International Conference on System Sciences, vol. 1, Jan. 1998, 13 pages.

Elkin et al., "Automated enhancement of description logic-defined terminologies to facilitate mapping to ICD9-CM", Journal of Biomedical Informatics Academic Press USA, vol. 35: Oct. 5-6, 2002, pp. 281-288.

Georgakopoulos et al., "An Overview of Workflow Management: From Process Modeling to Workflow Automatior Infrastructure", Distributed and Parallel Databases, vol. 3, No. 2, Apr. 1995, pp. 119-153.

Health Supplier, Retrieved from internet URL http://www.healthtrade.com/tw/en/left/healthsupplier-en.htm, 2000, 4 pages.

Healthcare informatics: Feb. 1999 News and Trends, Retrieved from internet URL: < http://www.healthcare-informatics.com/issues/1999/02_99/news.htm>, printed on, May 22, 2002, pp. 1-12.

Hogarth et al., "Terminology Query Language: A Server Interface For Concept-Oriented Terminology Systems", Proceedings of the AMIA Symposium. American Medical Informatics Association., 2000, 5 pages.

Horrocks, Ian, "Description Logic: Axioms and Rules", Dagstuhl Rule Markup Techniques, Feb. 7, 2002, pp. 1-51.

Ingenerf et al., "Standardized terminological services enabling semantic interoperability between distributed and heterogeneous systems", International Journal of Medicine Informatics, 2001, pp. 223-240.

Lowe et al., "The image engine HPCC project. A medical digital library system using agent-based technology to create an integrated view of the electronic medical record.", Digital Libraries, 1996. ADL'96., Proceedings of the Third Forum on Research and Technology Advances in. IEEE, 1996, May 13, 1996, pp. 45-56.

Marazakis et al., "Management of Work Sessions in Dynamic Open Environments", Proceedings Ninth International Workshop on Database and Expert Systems Applications, IEEE, Aug. 26-28, 1998, 6 pages.

Nielsen et al., "Using Domino Workflow.", IBM Corporation, International Technical Support Organization,, May 2000, pp. 148-178.

Nikolai et al., "Thesaurus federations: a framework for the flexible integration of heterogeneous, autonomous thesauri", Research and Technology Advances in Digital Libraries, 1998. ADL 98. Proceedings. IEEE International Forum on. IEEE, 1998, Apr. 22, 1998, pp. 46-55.

Non-Final Office Action received for U.S. Appl. No. 16/233,348, mailed on Oct. 26, 2022, 27 pages.

Non-Final Office Action received for U.S. Appl. No. 16/715,640, mailed on Jun. 9, 2022, 30 pages.

Noy et al., "Ontology Development 101: A Guide to Creating Your First Ontology", Web Page<{https://protege.stanford.edu/publications/ontology_development/ontology101.pdf>, Jul. 23, 2001, , retrieved from Internet Archive Wayback Machine <https://web.archive.org/web/20010801000000*/https://protege.stanford.edu/publications/ontology_development/onlology101.pdf> on Dec. 19, 2018, Dec. 19, 2018, pp. 1-20.

Organization Profile {Op Form), Retrieved from the internet URL http://www.unece.org/ceiproj/exlop.htm, 2002, 3 pages.

OWL, an ontology language, Ontogenesis, available at: <http://ontogenesis.knowledgeblog.org/55>, Jan. 21, 2010, pp. 1-6.

Preinterview First Office Action received for U.S. Appl. No. 16/233,341, mailed on Jul. 22, 2022, 4 pages.

Raths, David, "The Importance of Bringing EMS Systems Into the HIE Loop", Healthcare Informatics, Health It Summit Series., May 31, 2017, 3 Pages.

Rector et al., "A Terminology Server for Medical Language and Medical Information Systems", Published in the Proceedings IMIA WG6, Geneva, May 1994, May 1994, pp. 147-157.

Signature Product description information, Jun. 1985, 4 pages.

Taentzer et al., "Towards Refactoring of Rule-based, in-place Model Transformation Systems Taken", Available online at: <https://dl.acm.org/doi/10.1145/2432497.2432506>, 2021, pp. 41-46.

Yu et al., "Representing genomic knowledge in the UMLS semantic network", Proceedings of AMIA Annual Symposium The Emergence of Intemetable Health Care Systems That Really Work, Nov. 6, 1999, pp. 181-185.

Zhao et al., "Temporal Workflow Management in a Claim Handling System", ACM SIGSOFT Software Engineering Notes, vol. 24, No. 2, 1999, pp. 187-195.

Anonymous: "Database trigger", Retrieved from https://en.wikipedia.org/w/index.php?title=Database_trigger&oldid=1055502683, Nov. 16, 2021, pp. 1-7.

* cited by examiner

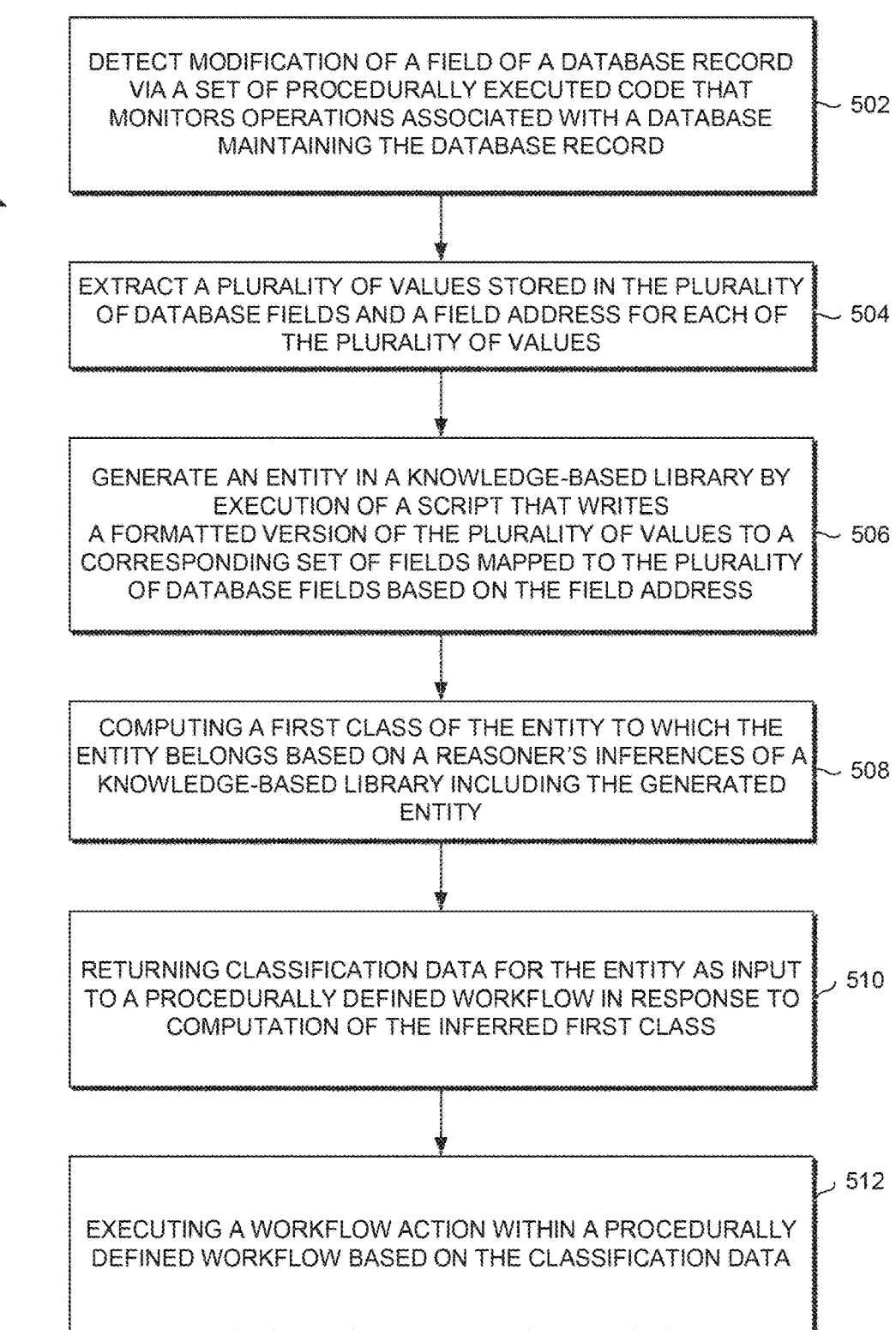

500

DETECT MODIFICATION OF A FIELD OF A DATABASE RECORD VIA A SET OF PROCEDURALLY EXECUTED CODE THAT MONITORS OPERATIONS ASSOCIATED WITH A DATABASE MAINTAINING THE DATABASE RECORD          502

EXTRACT A PLURALITY OF VALUES STORED IN THE PLURALITY OF DATABASE FIELDS AND A FIELD ADDRESS FOR EACH OF THE PLURALITY OF VALUES          504

GENERATE AN ENTITY IN A KNOWLEDGE-BASED LIBRARY BY EXECUTION OF A SCRIPT THAT WRITES A FORMATTED VERSION OF THE PLURALITY OF VALUES TO A CORRESPONDING SET OF FIELDS MAPPED TO THE PLURALITY OF DATABASE FIELDS BASED ON THE FIELD ADDRESS          506

COMPUTING A FIRST CLASS OF THE ENTITY TO WHICH THE ENTITY BELONGS BASED ON A REASONER'S INFERENCES OF A KNOWLEDGE-BASED LIBRARY INCLUDING THE GENERATED ENTITY          508

RETURNING CLASSIFICATION DATA FOR THE ENTITY AS INPUT TO A PROCEDURALLY DEFINED WORKFLOW IN RESPONSE TO COMPUTATION OF THE INFERRED FIRST CLASS          510

EXECUTING A WORKFLOW ACTION WITHIN A PROCEDURALLY DEFINED WORKFLOW BASED ON THE CLASSIFICATION DATA          512

MEMORY

612

PROCESSOR(S)

614

PRESENTATION
COMPONENT(S)

616

RADIO(S)

624

I/O PORT(S)

618

I/O COMPONENTS

620

POWER SUPPLY

622

610

SYSTEMS AND METHODS FOR ONTOLOGICALLY CLASSIFYING RECORDS

INCORPORATION BY REFERENCE; DISCLAIMER

Each of the following applications are hereby incorporated by reference: application Ser. No. 17/736,964 filed on May 4, 2022. The applicant hereby rescinds any disclaimer of claims scope in the parent application(s) or the prosecution history thereof and advises the USPTO that the claims in the application may be broader than any claim in the parent application(s).

TECHNICAL FIELD

Aspects hereof relate to devices, systems, and methods for classifying records based on asserted ontological axioms.

BACKGROUND

Traditional electronic health records (EHR) commonly utilize relational databases to organize and store patient records. These databases use structured and unstructured fields to hold values (e.g., numeric, descriptive, or illustrative) in any number of tables and nested tables. Although relational databases facilitate storage of massive amounts of data, complex querying traditionally called for writing each iteration of the query in procedural code. For example, decision support applications (e.g., patient care workflow automation applications) traditionally operate using computational algorithms that progress based on a complex querying schema.

BRIEF SUMMARY

In order for traditional computerized systems to aggregate and evaluate complex querying requests (e.g., a query that includes multiple inclusion criteria, exclusion criteria, or the combination of both) each iteration of the query is expressed as procedural code. The systems, methods, and devices described here present a paradigm shift from these traditional procedure-based constraints. In contrast to the traditional systems, those described herein facilitate hybrid procedure-based and ontology-based data evaluation. Among other benefits, the described systems, methods, and devices described herein may detect a triggering event, such as a modification of a field of a database record via a set of procedurally executed code that is monitoring operations associated with a database maintaining the database record. The database record may be relationally linked to a plurality of database fields including the field of the database record. A plurality of values stored in the plurality of database fields and a field address for each of the plurality of values may can be extracted from the database record by a procedurally executed portion of code (e.g., an object oriented script). In some aspects, an identifier may be extracted that links the database fields to the database record. Based on the extracted values, an entity is generated within a knowledge-based library by execution of a script that writes a formatted version of the plurality of values to a corresponding set of fields mapped to the plurality of database fields based on the field address. A class of the entity is computed based on inferences of a reasoner drawn from a knowledge-based library including the generated entity. In response to the computation of the entities class, classification data for the entity is returned as input to a procedurally defined workflow. The classification data may include at least a finding of a value of the plurality of values within the entity and a super class ontologically defined by the inferences reasoner drawn from a knowledge-based library including the generated entity. A workflow action may be executed within the procedurally defined workflow based on the classification data.

DESCRIPTION OF THE DRAWINGS

The present invention is described in detail herein with reference to the attached drawing figures, wherein:

FIG. 5 depicts an example method for hybrid procedure-based and ontology-based data evaluation, in accordance with aspects hereof.

DETAILED DESCRIPTION

Figure 1:
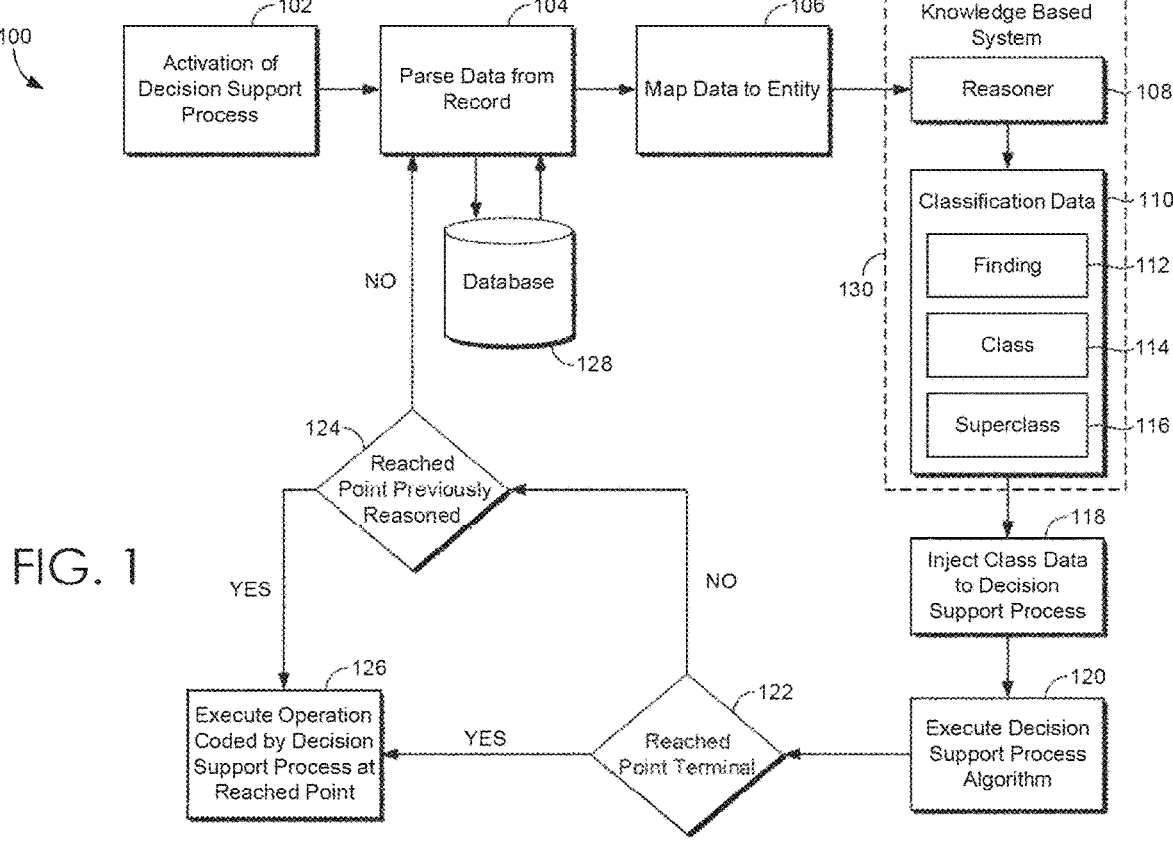
FIG. 1 depicts example process flow for a computerized system including for hybrid procedure-based and ontology-based data evaluation, in accordance with aspects hereof.

In order for a traditional computerized system to understand and aggregate the information stored in electronic records, the traditionally computerized system applied rules to evaluate the selected records. A separate rule is used to evaluate each possible combination of variables and values for each variable that may be present in the record. Thus, a separate rule is drafted to address each and every distinct combination of variable(s) and/or values(s) for each variable. For example, in order to evaluate records for one condition (e.g., variable) having multiple available states (e.g., a value), a rule is drafted for each distinct permutation of combinations that may be present in the record. As the amount of information stored in electronic records increases, the number and complexity of rules utilized escalates. For this reason, traditional computerized system require a vast number of rules.

To illustrate, in order for a traditional computerized system to aggregate and evaluate whether any of the plurality of records stored in a relational database support progression from a first point in a decision support workflow to a second point, a rule may be needed to evaluate each combination of the individual variable(s) and/or values(s). Generally, the decision point is a procedurally programmed step within the workflow where a set of rules define progression along one of at least two potential paths. A path may be simple (e.g., a closed loop or the programmatic equivalent of wait until the rules of the decision point are satisfied) or complex. In a traditional workflow, the two paths may include the algorithmic evaluation of data held in a database. As a simplified example, a traditional decision point can include an if/else programmatic expression. Where the conditions of the if expression are satisfied the workflow may advance along the path defined by the workflow. Otherwise, the workflow may advance along the path defined by the else expression of the workflow.

Even if a particular decision point only had five conditions where condition A has four available states, condition B has six available states, condition C has three available states, condition D has three available states, and condition E has four available states, the traditional computerized system may need to access and evaluate each one of the 864 available combinations by using 864 distinct rules. For example, a traditional patient care workflow to automate diagnosis of a viral infection may include procedural rules for each combination of lab values (e.g., oxygen saturation, cell count, antibody count, PCR result and so forth) and physical manifestation (e.g., temperature, inflammation, cough, and so forth) that are defined as necessary to verify the viral infection. Additionally, rules may be needed for each combination of the type of values that are possibly stored in the record. Moreover, traditional procedural code may include a rule that points to each combination of the potentially used fields a relational database. For example, a temperature value that may be stored in at different locations within the database based on the source of the temperature (e.g., oral, temporal, rectal, and so forth), the unit used to record the temperature (e.g., Celsius or Fahrenheit).

Further, differences between the structures of any two relational databases can prevent interoperability of the procedural code, because the particular field may be organized differently in the structure of each relational database. In other words, these procedurally coded rules may only enable evaluation of a single relational database structure, and thus a traditional computerized system cannot reuse procedurally coded rules for any relational database that does not adhere to one specific structure.

As such, a rules database consumes vast amounts of computer readable memory in order to store the supportive rules for record evaluations involving hundreds or thousands of conditions. Additionally, a significant amount of processing resources are utilized by the traditional computerized system in order to execute the rules against records for an evaluation involving hundreds or thousands of conditions. Further, each time that a change is made to one of the conditions or the available states for the conditions (e.g., new condition to add, a condition to remove, new state to add to a condition, or state to remove for a condition), the procedural code for the corresponding rules is modified to keep the rules database up-to-date.

The aspects described herein represent a paradigm shift away from procedural rule dependency. Rather, the aspects described herein may facilitate a hybridization of procedurally executed decision support and ontologically-based classification reasoning. In particular, the aspects described herein provide methods, systems, and media to facilitate automatic ingestion of variable(s) and/or values(s) relevant to one or more decision support workflows by a knowledge-based library. In some aspects, one or more scripts facilitate the automatic ingestion of the variable(s) and/or values(s). For example, a script may be executed that maps the location of database fields (e.g., a field address) of the variable(s) and/or values(s) called by the decision support workflow to a corresponding set of fields of an entity in the knowledge-based library. A reasoner may classify the variable(s) and/or values(s) based on the asserted relationships within the knowledge-based library and classification data maybe returned to facilitate computations defined by the one or more decision support workflows. The classification data may be a class, a direct super class, or indirect super class to which the generated entity belongs.

Turning to FIG. 1, an example process flow 100 including a procedural decision support workflow hybridized with a knowledge based classification system, in accordance with aspects described herein. The decision support workflow can be a diagnostic support workflow, an appointment scheduling support workflow, a billing support workflow, or any other workflow that includes procedurally programed algorithms that include an activation trigger (e.g., a programmatically detected action that initiates the workflow) and at least one decision point (e.g., a procedurally programed algorithm that evaluates data). Generally, process flow 100 facilitates the progression from a first point in a decision support workflow to a second point. In some aspects, the first point can be the activation trigger of the workflow and the second point can be a terminal or non-terminal decision point in the workflow.

Some embodiments of process flow 100 may begin with activation of the decision support process 102. Activation of the decision support process 102 may be triggered by any programmatically detected action that initiates the decision support workflow based on the process the workflow supports. For example, activation of the decision support workflow can be automatically triggered in response to the programmatic detection of a modification of a database record in some aspects. The modification of the database record can include addition of data to one or more fields of the database that is maintaining the database record. For example, and with brief reference to FIG. 3, the activation of the decision support process may be triggered by a decision support application 312 that is monitoring the operations of record database 320 maintained by record repository server 316. Activation of the decision support process workflow 102 can also be triggered in response to periodic, continuous, intermittent, or on-demand execution of the decision support workflow. For example, and with brief reference to FIG. 3, the activation of the decision support process may be triggered by periodic, continuous, intermittent, or on-demand execution of a workflow 314 maintained by the decision support application 312.

Some embodiments of process flow 100, data from a database record is parsed at block 104 based on the activated decision support workflow. The data maybe parsed from the database 128 using any suitable means. For example, in a particular aspect, a script is programmatically coded to extract the values stored in the database fields associated with the first decision point of the activated decision support workflow. In some embodiments, one of the extracted values corresponds to an identifier of the database record. The identifier may be an alphanumeric value that is associated with each of the fields of a database record. For example, the identifier may be a patient identification value, an index key value, or any other value that defines the relationship of a plurality of fields as belonging to the same database record. Additionally, a field address corresponding to each of the database fields that are holding the extracted values can be extracted at block 104. The field address can be a value that uniquely identifies the identity or location of the field in the database. A database record in the database may include multiple values in fields associated with a particular field address (e.g., multiple fields with a field address identified as holding temperature in Celsius).

Example process flow 100, at block 106, includes mapping the extracted data to an entity within a knowledge-based system. In some aspects the extracted data is mapped by execution of a script within a decision support application (e.g., decision support application 312 of FIG. 3). The script may include programmatic expressions that write a formatted version of field values to corresponding fields in an entity of the knowledge-based system. The script may additionally, or alternatively, communicate a formatted version of the field values to an ontology-guided classification component (e.g., ontology-guided classification component 302 of FIG.

3). For example, the script may determine the identity of each value extracted from the database based on the field address. Additionally, the script may include expressions that link the field address associated with the database to a field address of an entity in a knowledge-based system library. The script may further include expressions that convert the format of an extract value to the format native to the corresponding field within the entity. For example, the script may convert a value from a small integer field to floating point. For another example, the script may convert a variable string to a fixed string, a decimal to a floating point, or any other format conversion. Additionally, the script may include expressions that convert the value to a unit native to the corresponding field within the entity. For example, a value held in a field with a field address identified as holding temperatures in Celsius may be converted to Fahrenheit. For another example, a value held in a field identified as holding a date of birth may be converted to age in days, months, years, or any combination thereof.

In some aspects of process flow 100, block 106 includes creation of the entity within the knowledge-based system. For example, the script may include programmatic expressions that query the knowledge-based system for an entity corresponding to the identifier extracted from the database in block 104. Where the knowledge-based system includes an entity corresponding to the identifier, the script may modify the entity within the knowledge-based system with the other data extracted from database 128. In contrast, where the knowledge-based system does not include an entity corresponding to the identifier, the script may automatically execute operations that create a new entity within the knowledge-based system. In an aspect, the newly created entity is populated with at least one field that includes the identifier extracted from the database 128. Similarly, the script may facilitate the creation of the entity by communicating extracted data to an ontology-guided classification component (e.g., ontology-guided classification component 302 of FIG. 3).

Some aspects of process flow 100 include, at block 130, initiation of ontology-guided classification of an entity generated or modified at block 106 within a knowledge-based system. For example, a reasoner 108 may be activated to classify the entity based on the logical consequences of the data asserted in the entity. As depicted in FIG. 1, the output of reasoner 108 includes classification data 110. Classification data 110 includes at least one inferred classification of the entity stored within the knowledge-based library. In other words, and turning briefly to FIG. 3, the reasoner 108 accepts the rules, concepts, classes, and the relationships connecting each as defined by the data schema knowledge 304 and taxonomy knowledge 306 as true logical axioms. The reasoner 108 evaluates each entity in the library according to the rules and concepts, and infers which class 114 the entity belongs. For example, where the reasoner 108 infers that an entity contains data that belongs in an unconfirmed diagnostic class based on the asserted axioms, the reasoner 108 assigns the entity to the unconfirmed diagnostic class within the knowledge-based library. Similarly, reasoner 108 assigns the fields of the entity to a findings class 112 based on the asserted axioms in some aspects. For example, a temperature field with a value of 98.6 may be classified as belonging to the "normaltemperature" finding class. In contrast, a temperature field with a value of 102.7 may be classified as belonging to the "increasedtemperature" finding class. In other words, the reasoner 108 may classify the entity and the constituent fields of the entity based on the asserted axioms.

The reasoner 108 may output additional classification data in some aspects. For example, reasoner 108 may identify at least one super class 116 or direct super class of the entity or at least one filed based on the asserted axioms. A super class refers to any class that includes the inferred class ontological hierarchy. A direct super class refers to any class that is immediately above the inferred class in the ontological hierarchy.

Additionally, reasoner 108 can write data to a database or a file. In some aspects, the reasoner 108 writes data to a database or file in response to the classification of the entity. For example, the reasoner 108 may output the class to which the entity belongs, a super class to which the entity belongs, a direct super class to which the entity belongs, the classes to which the fields of the entity belong, the super classes to which the fields of the entity belong, the direct super classes to which the fields of the entity belong, or any combination thereof.

Some aspects of process flow 100 include, at block 118, communicating the classification data 110 to the decision support process. The communication of classification data 110 may be facilitated by at least one script in some aspects. For example, the script may include programmatic expressions that injects a formatted version of at least one piece of classification data to a field in the decision support workflow.

Some aspects of process flow 100 include, at block 120, executing the decision support process workflow algorithm based on the classification data. In some aspects, the decision support process workflow may progress, based on the classification data, to a first decision point in the workflow. For example, and with reference to FIG. 2, an example decision support process workflow 200 including decision points is provided, in accordance to aspects described herein. As depicted, decision support process workflow 200 may facilitates diagnostic responses to Covid-19. Example decision support process workflow 200 includes a triggering event at block 202, decision points 206 and 214, and terminal points 208, 210, 212, 216, 218, 220, 222, 224, and 226. The triggering event at block 202 activates the knowledge-based classification of the patient based on data held in the electronic health record (EHR) corresponding to the patient. The classification data is returned to the decision support process workflow algorithm and analyzed at block 204. In response, example decision support process workflow 200 proceeds to decision point 206.

At decision point 206, the classification data is analyzed based on the programmatically expressed algorithm associated with decision point 206. As illustratively depicted in FIG. 2, decision point 206 includes four possible paths. The patient may be evaluated by the decision point 206 as Covid-19 diagnosis confirmed, Covid-19 lab result positive, Covid-19 lab result negative, or no diagnosis or lab for Covid-19. Where analysis of the classification data corresponding to the patient entity satisfies at least one of the rules of the decision point 206, the example decision support process workflow 200 may proceed to the next procedural process of the workflow. For example, a patient evaluated as Covid-19 diagnosis confirmed, Covid-19 lab result positive, or Covid-19 lab result negative by decision point 206 progresses to terminal points 208, 210, or 212 respectively. In contrast, a patient evaluated as no diagnosis or lab for Covid-19 by decision point 206 progresses to decision point 214.

Figure 2:
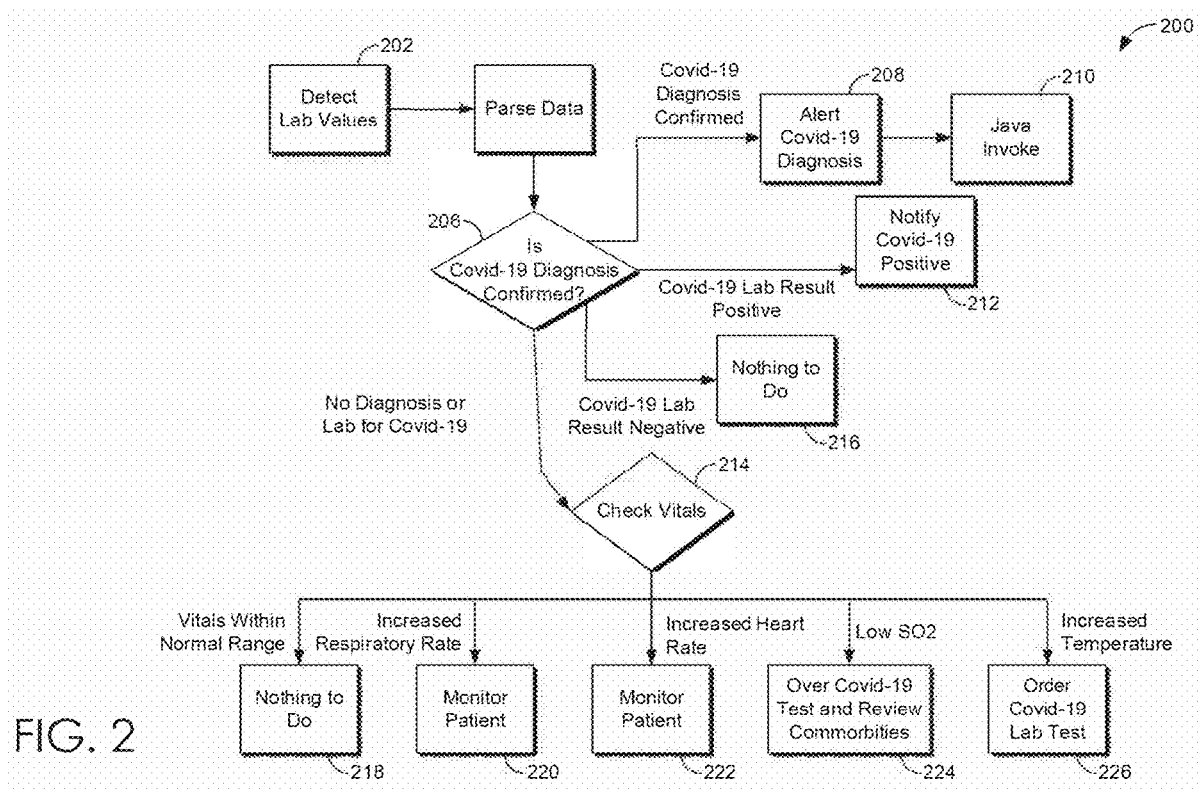
FIG. 2 depicts an example depiction of a procedurally defined workflow, in accordance with aspects hereof.

Returning to FIG. 1, and with continued reference to FIG. 2, some embodiments of flow 100 includes determining whether a terminal point is reached in the decision support process workflow at block 122. For example, a script may determine whether, based on the classification data, decision support process workflow 200 progressed to terminal points 208, 210, 212, 216, 218, 220, 222, or 224. Where the decision support process workflow progressed to a terminal point, flow 100 executes the operation coded by the decision support process workflow at the terminal point at block 126. For example, a decision support process workflow may modify a patient's record (e.g., database record) with a referral to a care provider, order a clinical intervention, or a script that triggers an alert when a portion of the database record is viewed via an application. Additionally, the decision support process workflow may among other things automatically initiate a different workflow or generate and communicate a request for information.

Alternatively, where the decision support process workflow progressed to a decision point (e.g., decision point 214) or any other non-terminal point in the workflow, process flow 100 processes to block 124. At block 124, process flow 100 determines whether the workflow reached the same point for the database record based on the same data parsed from the database record. For example, a script may assess a log file to determine whether decision support process workflow 200 has previously progressed to decision points 206 or 214 and was unable to continue. Further, the script may assess the log file and the database record to determine whether data was added to the patient's record (e.g., database record) since the decision support process workflow 200 progressed to decision points 206 or 214 and was unable to continue. In response to a determination that new data was added or the workflow has not progressed to the same point, block 124 may return to block 104. Alternatively, in response to a determination that no new data has been added and the workflow has progressed to the same point, block 124 may progress to block 126.

Figure 3:
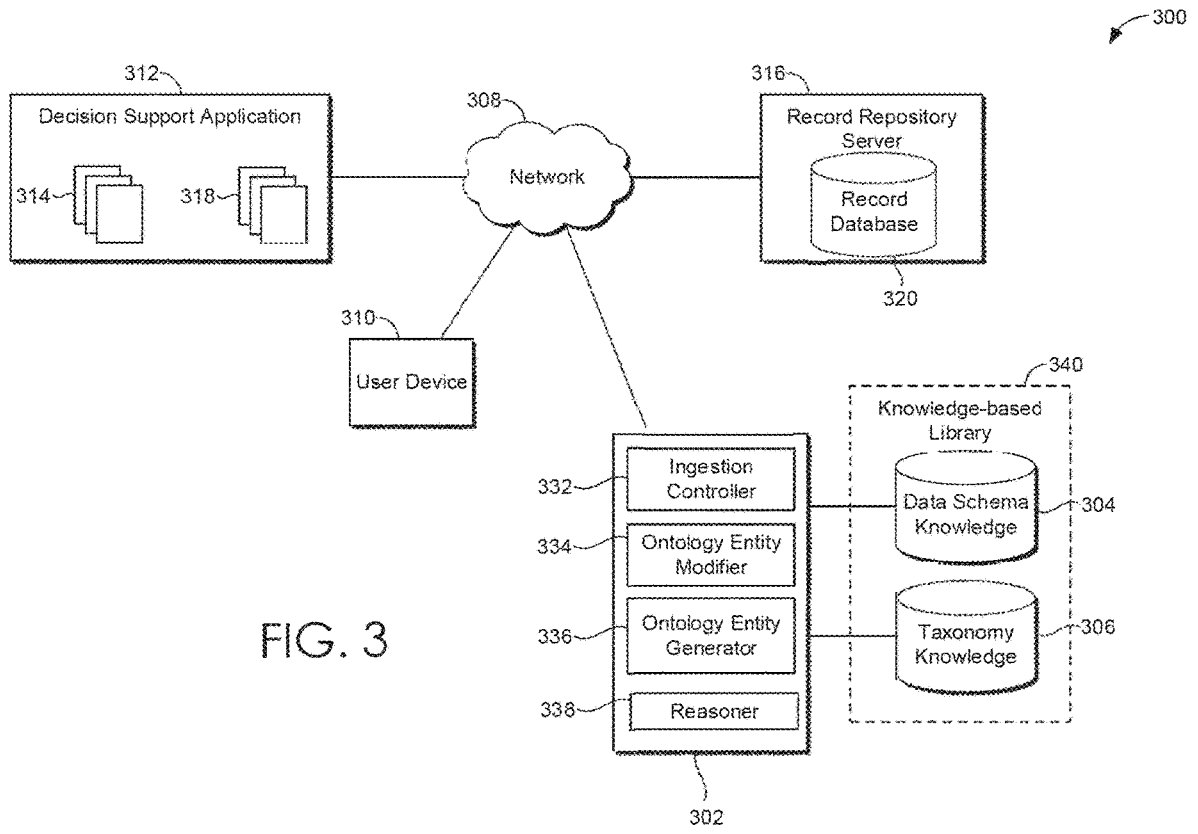
FIG. 3 depicts an example computing environment, in accordance with aspects hereof.

Turning to FIG. 3, an example system 300 including a procedural decision support hybridized with a knowledge-based classification system is depicted in accordance with aspects described herein. Generally, System 300 facilitates the execution of a procedurally coded decision support workflow (e.g., workflow 200 of FIG. 2) using classification data output from a knowledge-based ontology-guided processing environment 340. Some aspects of system 300 includes an ontology-guided classification component 302, network 308, at least one user device 310, a decision support application 312, and record repository server 316.

The ontology-guided classification component 302 may include hardware, software, firmware or any combination thereof. Additionally, some aspects of the ontology-guided classification component 302 can be a subroutine or sub-component of an application, cloud service, or any other computational platform. Generally, the ontology-guided classification component 302 receives queries from a decision support application 312 that hosts at least one procedurally coded decision support workflow 314 (e.g., workflow 200 of FIG. 2) and at least one procedurally coded script 318. The ontology-guided classification component 302 ingests data, generates entities, and reasons classifications based on ontological concepts and rules. The ontological concepts and rules are used to generate classification data (e.g., class, super class, direct super class, and finding) for entities. As such, some aspects of the ontology-guided classification component 302 includes an ingestion controller 332, an ontology entity modifier 334, an ontology entity generator 336, and a reasoner 338.

An ingestion controller 332 generally identifies queries that are submitted by the decision support application 312.

Ingestion controller 332 can identify queries in any suitable manner. For example, in some aspects, ingestion controller 332 may continuously, periodically, or intermittently crawl the decision support application's 312 for documents that contain data parsed from record repository server 316. In other aspects, ingestion controller 332 monitors data communicated from decision support application 312 and analyzes the data to identify data parsed from record repository server 316. In some aspects, ingestion controller 332 compares an identifier included in the data to a set of identifiers stored in a lookup table to determine whether an entity corresponding to the identifier is new or has been previously processed in the knowledge-based environment 340. When the ingestion controller 332 detects that an entity containing the identifier does not exist within a knowledge-based library, the ingestion controller 332 activates an ontology entity generator, such as ontology entity generator 336. Additionally, or alternatively, when the ingestion controller 332 detects an entity within the knowledge-based library that includes the identifier within a field, the ingestion controller 332 activates an ontology entity modifier, such as ontology entity modifier 334.

Ontology entity modifier 334 generally accepts formatted versions of values from a script, and outputs machine-readable modifications to preexisting entities within a knowledge-based library (e.g., knowledge-based library 340). The modifications may include the addition of values to previously unpopulated data fields, replacement of values in previously populated data fields, removal of values in previously populated data fields, addition of values to new instances of previously populated data fields, or any other computer understandable data manipulation function. The values may be mapped to data fields of the entity based on data encoded by a script (e.g., script 318). Ontology entity modifier 334 comprises a module within a software application, a software application, or set of applications (which may include programs, routines, functions, or computer-performed services) that is executed by a processor associated with the ontology-guided classification component 302

Ontology entity generator 336 generally accepts formatted versions of values from a script, and outputs a machine-readable entity within a knowledge-based library (e.g., knowledge-based library 340). The values may be mapped to data fields of the entity based on data encoded by a script (e.g., script 318). Ontology entity generator 336 comprises a module within a software application, a software application, or a set of applications (which may include programs, routines, functions, or computer-performed services) that is executed by a processor associated with the ontology-guided classification component 302.

Reasoner 338 generally infers the logical consequences of an asserted patient entity. The output of reasoner 338 includes an inferred classification of each record (e.g., the asserted patient entity) stored in a record database (e.g., record database 320) based on the knowledge-based library. In other words, the reasoner 338 accepts the rules, concepts, classes, and the relationships connecting each as true logical axioms. As is discussed in more detail with reference to FIG. 4, the reasoner 338 evaluates the values of each entity in a knowledge-based library (e.g., knowledge-based library 340) according to the rules and concepts, and infers in which class the entity belongs. For example, when the reasoner 338 infers that an entity contains values that, based on the asserted axioms of the knowledge-based library, belongs in an asserted class (e.g., classes 404 of FIG. 4) the reasoner 338 assigns that record to the asserted class. As such, the inferences of reasoner 338 for an entity may be dependent on the knowledge-based library and the values included in the entity. The modification of a value within an entity may result in reasoner 338 reclassifying the entity. Similarly, the modification of the concepts, rules, or relationships of a class, or the addition of a class, may result in reasoner 338 reclassifying the entity. In other words, the classification of an entity is dynamically dependent on the values associated with the entity.

Additionally, reasoner 338 can infer the finding of one or more values within each entity. The finding may be inferred by reasoner 338 based on the concepts, rules, and relationships asserted within knowledge-based library. For example, a value in a field corresponding to temperature greater than a predetermined threshold may have a finding of IncreasedTemperature. Similarly, a value less than or equal to the predetermined threshold may have a finding of NormalTemperature. In some aspects, the reasoner 138 writes data to a database or file in response to the determination that a patient record belongs to a predetermined class. In some aspects, the particular database record or particular file the data is written to varies based on the class to which the patient record is assigned. Example reasoners include Cyc, KAON2, Cwm, Drools®, Flora-2, Jena, Prova.

In some aspects, an ontology-guided classification component 302 is communicatively coupled to a knowledge-based library 340. Generally, a knowledge-based library maintains a plurality of rules, concepts, relationships, and the taxonomy asserted as true. Further, a knowledge-based library can maintain one or more entities. The entities may be populated into the knowledge-based library by an ontology-guided classification component 302, a script 318, or a combination of both in some aspects. The entities included in the knowledge-based library include a plurality of data fields including at least an identifier that corresponds to an identifier of a database record maintained by a record database (e.g., record database 320). The values of the entity are asserted as true. However, the class of the entity is not asserted as true in at least one aspect. Rather, the class of an entity is inferred based on the rules, concepts, relationships, and the taxonomy asserted as true in the knowledge-based library 340. The knowledge-based library may be maintained by one or more servers and one or more databases. As depicted in FIG. 3, example knowledge-based library 340 includes data schema knowledge database 304 and a taxonomy knowledge database 306.

Data schema knowledge database 304 stores and maintains one or more data schema knowledge libraries. A data schema knowledge library comprises a computer-understandable model of all of the domain knowledge associated with a data schema. For example, a data schema knowledge library includes the field nomenclature, field types, metadata, domain resources, field addresses, and other similar framework rules. Similarly, taxonomy knowledge database 306 stores and maintains one or more taxonomy knowledge libraries. A taxonomy knowledge library comprises a computer-understandable model of all of the domain knowledge associated with a taxonomy. For example, in some aspects, taxonomy knowledge database 306 includes a SNOMED CT library.

Network 308 generally facilitates communication between the ontology-guided classification component 302, user device 310, record repository server 316, other devices or servers connected to network 308, or any combination thereof. As such, network 308 can include access points, routers, switches, or other commonly understood network components that provide wired or wireless network connectivity. In other words, network 308 may include multiple networks, or a network of networks, but is depicted in a simple form so as not to obscure aspects of the present disclosure. By way of example, network 308 can include one or more wide area networks (WANs), one or more local area networks (LANs), one or more public networks, such as the Internet, one or more private networks, one or more telecommunications networks, or any combination thereof. In other words, where network 308 includes a wireless telecommunications network, components such as a base station, a communications tower, or even access points (as well as other components) may provide wireless connectivity. Networking environments are commonplace in enterprise-wide computer networks, intranets, and the Internet. Accordingly, network 308 is not described in significant detail herein.

System 300 includes a user device 310. User device 310 generally facilitates a user's (i.e., user of the device) interaction with the output of ontology-guided classification component 302 and decision support application 312. Additionally, user device 310 can facilitate access to a record repository server 316. User device 310 can facilitate this interaction by executing an application stored in computer-readable media that allows the user device 310 to communicatively couple with the ontology-guided classification component 302, record repository server 316, or both. Alternatively, user device 310 can locally execute some or all of the components of the ontology-guided classification component 302, though not shown in such a configuration in FIG. 3. The application may include operational modules that can utilize a combination of hardware, firmware, and computer executable instructions. The application may include any number of other elements that facilitate communicating with the ontology-guided classification component 302, record repository server 316, or any combination thereof, such as account login, encryption and decryption protocols, and so forth. For example, the application may be a locally executed EHR client, a cloud based EHR client, an EHR web portal, a mobile EHR app, or any other suitable application. An illustrative example of an EHR client application includes, but is not limited to, Cerner's® Millennium®, PowerChart®, and PowerTrials®. Some aspects of user device 310 include some or all of the components of computing device 500 discussed in relation to FIG. 5.

System 300 includes a decision support application 312 that facilitates execution of procedurally coded workflows 314. The hosted workflows 314 can be in any format suitable to store procedural code. In a particular aspect, each workflow, such as workflows 314, contains code that corresponds to a diagnostic decision support tool. As depicted in FIG. 2, an example workflow can be programmatically coded to assist the diagnosis and treatment of viral infections, such as COVID-19. However, it will be understood that this is merely an example of a procedurally coded workflow. For example, the decision support application may assist diagnosis, treatment, scheduling of patients, or any combination thereof. In an aspect, execution of the decision support application based on classification data provides information related to one or more of: determining the effect of one or more drugs, determining the effect of one or more medical interventions, supporting extubating the patient, suggesting extubating the patient, supporting adjustment of patient therapy, supporting an adjustment to medication, suggesting an adjustment to patient therapy, supporting ventilator settings, suggesting adjusting ventilator settings, weaning the patient off ventilation, suggesting weaning the patient off ventilation, assessing patient status before surgery, assessing patient status during surgery, assessing patient status after surgery, assessing patient status before a medical procedure, assessing patient status during a medical procedure, assessing patient status after a medical procedure, monitoring for air leaks, monitoring for improper ventilation, monitoring exercise, monitoring stress levels, monitoring a medical condition, or monitoring a disease.

Decision support application 312 may also maintain one or more scripts 318. Script 318 can include programmatic code to extract values stored in database fields of a record maintained by a record database (e.g., record database 320). Additionally, the script(s) 318 may extract field addresses associated with each value extracted from the record. Further, the script(s) 318 may include expressions that link the field address associated with the database to a corresponding field address of an entity in a knowledge-based system library. The script(s) 318 may further include expressions that convert the format of an extracted value to the format native to the corresponding field within the entity. For example, script(s) 318 may convert a value from a small integer field to floating point. For another example, the script may convert a variable string to a fixed string, a decimal to a floating point, or any other format conversion. Additionally, the script(s) 318 may include expressions that convert the value to a unit native to the corresponding field within the entity. For example, a value held in a field with a field address identified as holding temperatures in Celsius may be converted to Fahrenheit. For another example, a value held in a field identified as holding a date of birth may be converted to age in days, months, years, or any combination thereof. The script(s) 318 may include computer executable procedural code in any suitable format. For example, script(s) 318 may include json, java, C++, C#, Python, R, PHP, Visual Basic.NET, JavaScript, Ruby, Perl, SIM-SCRIPT, Object Pascal, Objective-C, Dart, Swift, Scala, Kotlin, Common Lisp, MATLAB, or Smalltalk files in some aspects.

System 300 also includes a record repository server 316, mentioned above. The record repository server 316 generally facilitates the storage and maintenance of data. Generally, the data can be stored via any suitable computer-readable media communicatively accessible to the processing components of the record repository server 316. For example, the data can be stored in a record database 320 with a defined data schema. As will be understood by those skilled in the art, the data schema of a record database (e.g., record database 320) can vary widely. For example, the nomenclature, table structure, field structure, and database language (e.g., SQL, Oracle, SQL Server, MySQL, and so forth) preferred by the person or people building and administrating the database directly and indirectly affect the overall data schema.

Record repository server 316 generally maintains one or more record databases 320 that store and organize data records. Record repository server 316 can include hardware, software, firmware that facilitate creation, retrieval, and modification of the data records stored in the record database 320. Each database 320 has a data schema. The data schema includes the relational associations, metadata, and configuration of each field and table of database 320. In some aspects, record repository server 316 comprises an EHR system. An EHR system includes medical records, which may be maintained in one or more databases, and may further include one or more computers or servers that facilitate the storing and retrieval of the medical records associated with a patient. Each medical record contains personal medical or health data for a particular patient and any other data associated with the patient (e.g., a unique identifier, demographic data, scheduled appointments, care facility admission information, and so forth). Examples of EHR systems include Cerner's® Millennium®. In some aspects, record repository server 316 also includes an interoperability interface, which is a computing interface that enables data transmission between the database 320 and another device (e.g., user device 310, ontology-guided classification component 302, decision support application 312, or any other device). In particular, the interoperability interface may define how calls, codes, or requests are made in the data schema used by the record database 320 that is maintained by the record repository server 316.

It should be understood that the system 300 of FIG. 3 is one suitable example of the arrangement of components. Other components not shown may be included or omitted, in various aspects. In addition, each of the components may be implemented via a single device or multiple devices, such that the quantity shown in FIG. 3 is a non-limiting example.

In a traditional computerized system, a computer programmer would convert the diagnostic criteria included in a standard of care, predicative model, or standard procedure into procedural code that identifies each iteration of the diagnostic criteria. As mentioned above, even relatively uncomplicated diagnostic criteria can result in a significant number of possible permutations. For example, particular diagnostic criteria having only had five inclusion criteria conditions where condition A has four available states, condition B has six available states, condition C has three available states, condition D has three available states, and condition E has four available states, may have 864 available permutations (i.e., 4×6×3×3×4=available permutations of the available states). Moreover, a single misplaced ',' or ';' or '(' or ')' in any of the procedural code permutations may result in inoperable procedural code or improperly operating procedural code. Because each procedural code permutation includes a state for each condition based on the unique criteria for the diagnosis; reusing or repurposing procedural code created for one clinical trial with the criteria of another clinical trial is traditionally a non-option.

Figure 4:
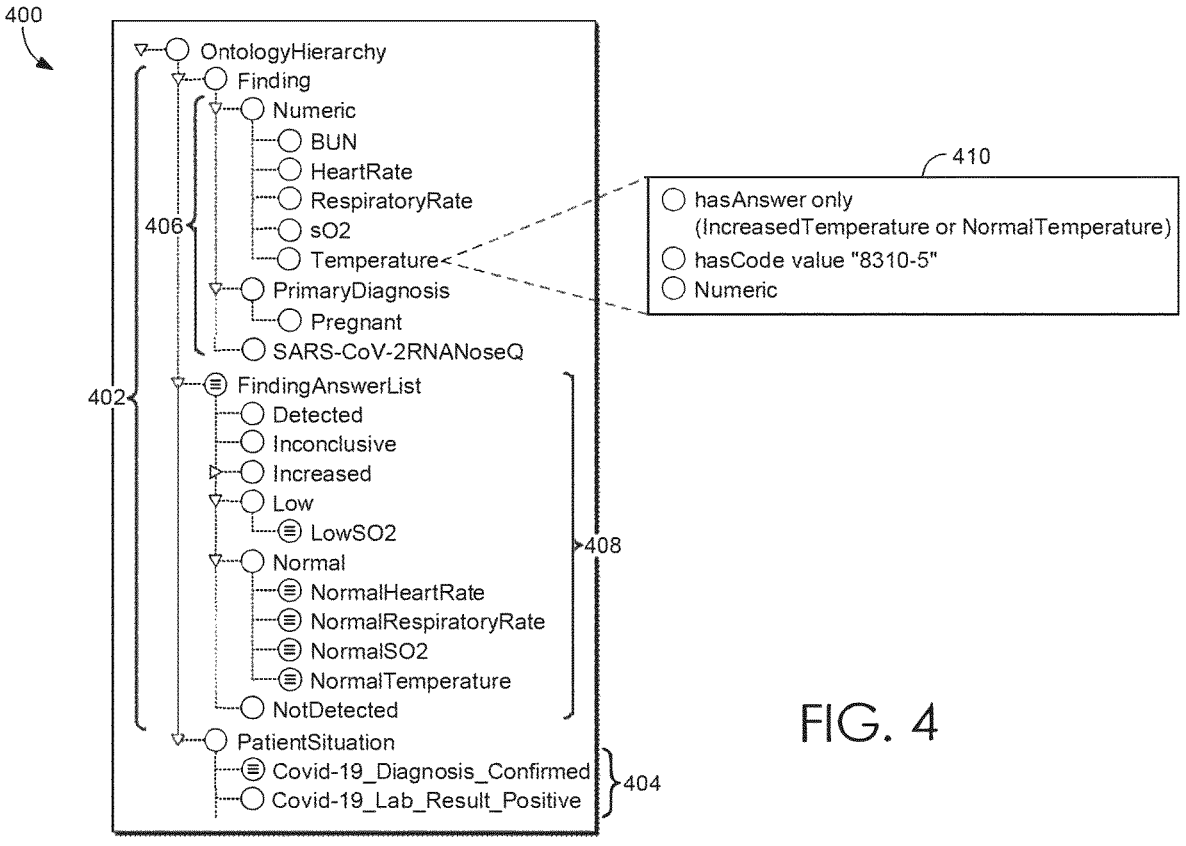
FIG. 4 depicts an example ontology hierarchy, in accordance with aspects hereof.

In contrast, with reference to FIG. 4 and with continued reference to FIG. 3, using a knowledge-based library with an ontology hierarchy (e.g., ontology hierarchy 400) and the systems and methods described herein significantly reduces or eliminates the need for customized procedural code to query a database of records to facilitate a procedural coded workflow maintained by a decision support application (e.g., decision support application 312). FIG. 4 depicts an example ontology hierarchy 400, in accordance with aspects described herein. The depicted example ontology hierarchy 400 is a representative portion of the hierarchy that may be generated by an ontology-guided classification component (e.g., ontology-guided classification component 302 of FIG. 3) from a knowledge-based library (e.g., knowledge-based library 340).

Similar to ontologies in other scientific and technical fields, an ontology hierarchy (e.g., ontology hierarchy 400) comprises a "tree", "backbone", or "hierarchy" representing the relationships of the concepts and rules 402 and classes 404. For example, the depicted concepts 406 include a group of numeric concepts including a Temperature concept. Each concept 406 is linked to at least one rule 408 by a set of properties 410. Properties of a concept are the characteristics of the concept. The characteristics can include directed binary relations that specify a rule which is true for instances of that concept, logical features, for example, by being transitive, symmetric, inverse and functional. For example, in the ontology hierarchy 400, the depicted properties 410 specify that the Temperature concept can have an answer that is defined by the rules defined by IncreasedTemperature rule or the NormalTemperature rule. Further, properties can include interoperability data schema associations. For example, in the ontology hierarchy 400, the Temperature concept has a property 410 that associates the Temperature concept with a particular FHIR® code (e.g., field address, 8310-5).

The ontology hierarchy reference rules in relation to concepts and classes, as mentioned above. Rules 308 define the directed binary relations, logical expression, or a combination thereof that is asserted as true for an entity. Said another way, for each entity analyzed, a reasoner (e.g., reasoner 338) assumes that the finding answer for the Temperature concept is IncreasedTemperature if the rule IncreasedTemperature is true when evaluated with the temperature data (e.g., value stored in the data field) included in the entity.

The ontology hierarchy reference classes in relation to concepts and rules, as mentioned above. A class is the logical axiom that describes an entity based only on the rules and concepts of the ontology hierarchy. An ontology hierarchy may include one or more asserted classes. Each class is defined by a relationship to the applicable concepts. For example, the ontology hierarchy 400 includes two depicted classes 404 (i.e., Covid-19_Diagnosis_Confirmed and Covid-19_Lab_Result_Positive). A reasoner will infer that an entity is a member of Covid-19_Diagnosis_Confirmed class if, for example, the entity includes value data that makes the logical axiom for that class true. Although FIG. 4 depicts two classes, an ontology hierarchy can include a plurality of classes Continuing, FIG. 5 depicts an example method 500 for integrating knowledge-based classification data of an entity (e.g., a patient record) with a procedurally coded decision support workflow, in accordance with aspects described herein. For example, Aspects of method 500 can facilitate a procedurally coded workflow (e.g., workflow 200 of FIG. 2) maintained by a decision support application (e.g., decision support application of FIG. 3) based on classification data generated by inferences from an ontology-guided classification component (e.g., ontology-guided classification component 302 of FIG. 3) and a knowledge-based library (e.g., knowledge-based library 340 of FIG. 3). Aspects of method 500 can be carried out by a processor executing instructions stored in computer-readable media. The processor can carry out the instructions using any combination of hardware, firmware, or software directly or indirectly accessible by the processor. For example, some aspects of method 500 can be implemented by an ontology-guided classification component 302, as described in relation to FIG. 3.

Generally, method 500 detects a triggering event (e.g., a modification of a database record or execution of a procedurally coded decision support workflow). A set of values, field addresses, and an identifier are extracted for a database record. The extracted data is populated into an entity within an knowledge-based library. The rules, concepts, and relationships of the knowledge-based library are asserted by a reasoner to infer the class of the entity. Based on the inferred class, classification data of the entity and the values within the entity are computed. The classification data is returned to a procedurally coded decision support workflow, which is executed based on the classification data.

Some aspects of method 500 begin with block 502. At block 502, a modification of a field of a database record is detected via a set of procedurally executed code that monitors operations associated with a database maintaining the database record. For example, a script (e.g., script 318 of FIG. 3) crawls or queries record repository server (e.g., record repository server 316 of FIG. 3) for changes to the record database (e.g., record database 320 of FIG. 3) in some aspects. The crawl or query can be continuous, periodic, or intermittent. Additionally or alternatively, repository server 316 can push newly modified records to a decision support application the ingestion controller.

Some aspects of method 500 alternatively begin with detection of a triggering event. For example, a procedurally coded workflow (e.g., procedurally coded workflow 318 of FIG. 3) can be executed to continuously, periodically, intermittently, or on demand within a decision support application (e.g., decision support application 312 of FIG. 3). The workflow may be executed, by for example, commands issued by a user device (e.g., user device 310 of FIG. 3). For example, a user may access a patient record held in the record repository via interaction with an EHR application interface. In response, the EHR application interface may activate one or more workflows via commands transmitted to the decision support application. The execution of the workflow may activate one or more scripts that query the database record for the patient.

At block 504, a plurality of values stored in database fields are extracted from the database record. The values include at least an identifier corresponding to the database record. Additionally, in some aspects, a field address is extracted for the database field associated with each of the plurality of values. For example, a script (e.g., script 318 of FIG. 3) is procedurally coded to extract the values and corresponding field addresses for one or more database records maintained by a database (e.g., record database 320).

At block 506, an entity is generated in a knowledge-based library by execution of a script that writes a formatted version of the plurality of values to a corresponding set of fields mapped to the plurality of database fields based on the field address. Some aspects of block 506 may be facilitated by the executable procedural code of a script (e.g., script 318 of FIG. 3), an ingestion controller (e.g., ingestion controller 332 of FIG. 3), an ontology entity generator (e.g., ontology entity generator 336 of FIG. 3), or any combination thereof. For example, in a particular aspect, the script includes a computer readable map of the field address from the record database (e.g., record database 320 of FIG. 3) to a corresponding set of field addresses in entities of the knowledge-based library. The script may communicate the identifier(s) extracted from the record database with the ingestion controller. The ingestion controller may query the knowledge-based library for an entity (or entities) including the identifier(s) as a value within a data field. In response to a negative query result (i.e., the query returns no entities), the ingestion controller activates an ontology entity generator (e.g., ontology entity generator 336 of FIG. 3). The entity may be generated by the ontology entity generator with the values extracted by the script in data fields defined by the mapping encoded within the script. Alternatively, some aspects of block 504 include modifying a preexisting entity within the knowledge-based library in response to detection of an entity (or entities) including the identifier(s) extracted by the script. An ingestion controller may activate an ontology entity modifier (e.g., ontology entity modifier 334 of FIG. 3). The entity may be modified to include the values extracted by the script in data fields defined by the mapping encoded within the script.

At block 508, a first class of the entity to which the entity belongs is computed based on the inference of a reasoner and a knowledge-based library including the entity. Aspects of block 508 are facilitated by a reasoner (e.g., reasoner 338 of FIG. 3) and a knowledge-based library (knowledge-based library 340 of FIG. 3). For example, a reasoner may be activated to classify the entity based on the logical consequences of the data asserted in the entity. The output of reasoner may include at least one inferred class of the entity stored within the knowledge-based library. In other words, the reasoner accepts the rules, concepts, classes, and the relationships connecting each as defined by the data schema knowledge and taxonomy knowledge as true logical axioms. The reasoner evaluates each entity in the library according to the rules and concepts, and infers which class the entity belongs.

At block 510, classification data is returned as input to a procedurally defined workflow for the entity in response to determination of the inferred class. The classification data may include the first class, one or more super classes of the first class, one or more direct super classes of the first class, one or more findings of the values within the entity, or any combination thereof. In some aspects, block 510 is facilitated by a reasoner (e.g., reasoner 338 of FIG. 3) and a knowledge-based library (knowledge-based library 340 of FIG. 3).

At block 512, a workflow action within a procedurally defined workflow is executed based on the classification data. In some aspects, block 512 is facilitated by a decision support application (e.g., decision support application 312 of FIG. 3), a user device (e.g., user device 310 of FIG. 3), or a combination of both. Additionally, some aspects of block 512 reinitiate one or more portions of method 500 where execution of the procedurally defined workflow reaches a non-terminal point of the procedurally defined workflow. For example, as discussed in relation to FIGS. 1 and 2, during or after execution of the procedurally defined workflow based on the classification data, the decision support application may trigger a script to determine if the workflow reached a terminal point. Where a terminal point is not reach, the decision support application may trigger a script to extract additional data from the database record. The class of the entity corresponding to the database record may be populated with the additional data and the class of the entity may be re-inferred by the reasoner.

Advantageously, and in contrast to traditional procedurally defined workflows, the class of an entity is dynamically dependent on the values associated with the entity. As such, and again in contrast to traditional procedurally defined workflows, the addition or manipulation of data within a record may not merely advance the workflow to the next procedurally defined point. Rather, aspects of the hybridized systems and methods described herein may facilitate adaptive execution of a procedurally defined workflow based on the classification data dynamically inferred based on the rules, classes, and relationships defined by a knowledge-based library.

Embodiments of the disclosure may be described in the context of computer code or machine-useable instructions, including computer-useable or computer-executable instructions, such as program modules, being executed by a computer or other machine, such as a personal data assistant, a smartphone, a tablet PC, or other handheld device. Generally, program modules, including routines, programs, objects, components, data structures, and the like, refer to code that performs particular tasks or implements particular abstract data types. Embodiments of the disclosure may be practiced in a variety of system configurations, including mobile devices, consumer electronics, more specialty computing devices, or the like. Embodiments of the disclosure may also be practiced in distributed computing environments where tasks are performed by remote-processing devices that are linked through a communications network. In a distributed computing environment, program modules may be located in both local and remote computer storage media including memory storage devices.

Figure 6:
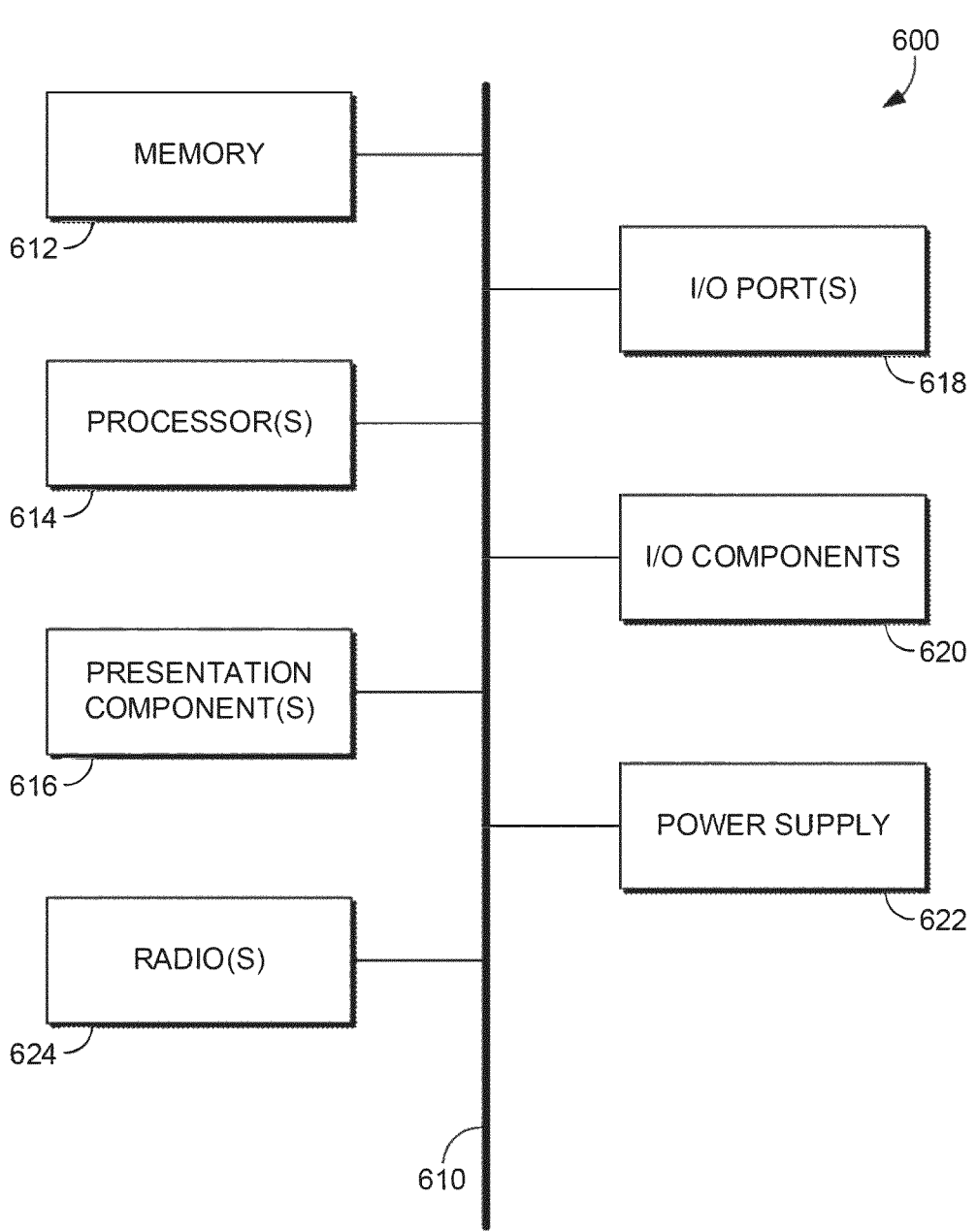
FIG. 6 depicts an example computing device, in accordance with aspects hereof.

With reference to FIG. 6, computing device 600 includes a bus 610 that directly or indirectly couples the following devices: memory 612, one or more processors 614, one or more presentation components 616, one or more input/output (I/O) ports 618, one or more I/O components 620, and an illustrative power supply 622. Bus 610 represents what may be one or more busses (such as an address bus, data bus, or combination thereof). Although the various blocks of FIG. 6 are shown with lines for the sake of clarity, in reality, these blocks represent logical, not necessarily actual, components. For example, one may consider a presentation component such as a display device to be an I/O component. In addition, processors have memory. The inventors hereof recognize that such is the nature of the art and reiterate that the diagram of FIG. 6 is merely illustrative of an exemplary computing device that can be used in connection with one or more embodiments of the present disclosure. Distinction is not made between such categories as "workstation," "server," "laptop," "handheld device," etc., as all are contemplated within the scope of FIG. 6 and with reference to "computing device."

Computing device 600 typically includes a variety of computer-readable media. Computer-readable media can be any available media that can be accessed by computing device 600 and includes both volatile and nonvolatile media, removable and non-removable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules, or other data. Computer storage media includes, but is not limited to, RAM, ROM, EEPROM, flash memory or other memory technology, CD-ROM, digital versatile disks (DVDs) or other optical disk storage, magnetic cassettes, magnetic tape, magnetic disk storage or other magnetic storage devices, or any other medium which can be used to store the desired information and which can be accessed by computing device 600. Computer storage media does not comprise transitory signals per se. Communication media typically embodies computer-readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media, such as a wired network or direct-wired connection, and wireless media, such as acoustic, RF, infrared, and other wireless media. Combinations of any of the above should also be included within the scope of computer-readable media.

Memory 612 includes computer storage media in the form of volatile and/or nonvolatile memory. The memory may be removable, non-removable, or a combination thereof. Exemplary hardware devices include solid-state memory, hard drives, optical-disc drives, etc. Computing device 600 includes one or more processors 614 that read data from various entities such as memory 612 or I/O components 620. Presentation component(s) 616 presents data indications to a user or other device. Exemplary presentation components include a display device, speaker, printing component, vibrating component, and the like.

The I/O ports 618 allow computing device 600 to be logically coupled to other devices, including I/O components 620, some of which may be built in. Illustrative components include a microphone, joystick, game pad, satellite dish, scanner, printer, wireless device, etc. The I/O components 620 may provide a natural user interface (NUI) that processes air gestures, voice, or other physiological inputs generated by a user. In some instances, inputs may be transmitted to an appropriate network element for further processing. An NUI may implement any combination of speech recognition, touch and stylus recognition, facial recognition, biometric recognition, gesture recognition both on screen and adjacent to the screen, air gestures, head and eye tracking, and touch recognition associated with displays on the computing device 600. The computing device 600 may be equipped with depth cameras, such as stereoscopic camera systems, infrared camera systems, RGB camera systems, and combinations of these, for gesture detection and recognition. Additionally, the computing device 600 may be equipped with accelerometers or gyroscopes that enable detection of motion. The output of the accelerometers or gyroscopes may be provided to the display of the computing device 600 to render immersive augmented reality or virtual reality.

Some embodiments of computing device 600 may include one or more radio(s) 624 (or similar wireless communication components). The radio 624 transmits and receives radio or wireless communications. The computing device 600 may be a wireless terminal adapted to receive communications and media over various wireless networks. Computing device 600 may communicate via wireless protocols, such as long term evolution ("LTE"), code division multiple access ("CDMA"), global system for mobiles ("GSM"), or time division multiple access ("TDMA"), as well as others, to communicate with other devices. The radio communications may be a short-range connection, a long-range connection, or a combination of both a short-range and a long-range wireless telecommunications connection. When we refer to "short" and "long" types of connections, we do not mean to refer to the spatial relation between two devices. Instead, we are generally referring to short range and long range as different categories, or types, of connections (i.e., a primary connection and a secondary connection). A short-range connection may include, by way of example and not limitation, a Wi-Fi® connection to a device (e.g., mobile hotspot) that provides access to a wireless communications network, such as a WLAN connection using the 802.11 protocol; a Bluetooth® connection to another computing device is a second example of a short-range connection, or a near-field communication connection. A long-range connection may include a connection using, by way of example and not limitation, one or more of CDMA, LTE, GPRS, GSM, TDMA, and 802.16 protocols.

The subject matter of the technology described herein is described with specificity to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of the methods employed, the terms should not be interpreted as implying any particular order among or between various steps herein disclosed unless and except when the order of individual steps is explicitly described. Additionally, those skilled in the art will understand that the pseudocode included herein, is illustrative in nature and given the variations programmatic languages should not be interpreted as implying any particular requirements.

What is claimed is:

1. A computer-implemented method performed by one or more hardware processors, the computer-implemented method comprising:

detecting modification of a field, of a plurality of database fields, for a database record via a set of procedurally executed code that is monitoring operations associated with a database maintaining the database record;

responsive to detecting the modification of the field:

extracting, via the set of procedurally executed code, a plurality of values stored in the plurality of database fields for the database record, wherein the plurality of values comprises an identifier;

determining an electronic entity based on one or both of the identifier extracted via the set of procedurally executed code and the plurality of values, the electronic entity comprising a plurality of entity-data fields;

updating the plurality of entity-data fields, of the electronic entity, based on the plurality of values extracted from the plurality of database fields by the set of procedurally executed code;

subsequent to updating the plurality of entity-data fields of the electronic entity, computing a first class of the electronic entity based on inferences of a reasoner, drawn from a knowledge-based library based at least in part on the plurality of entity-data fields of the electronic entity;

returning classification data, corresponding to the first class, for the electronic entity as input to a procedurally defined workflow; and executing a workflow action within the procedurally defined workflow based on the classification data.

2. The computer-implemented method of claim 1, and further comprising determining, by the reasoner, a medical diagnostic class, wherein the electronic entity is determined to belong to the medical diagnostic class based on logical consequences of a plurality of health data values associated with the electronic entity, and wherein the classification data comprises the medical diagnostic class.

3. The computer-implemented method of claim 1, wherein the classification data indicates a diagnosis of the electronic entity and is returned as input to the procedurally defined workflow.

4. The computer-implemented method of claim 3, further comprising executing the workflow action within the procedurally defined workflow using the classification data.

5. The computer-implemented method of claim 1, wherein detecting modification of the field corresponds to determining via the one or more hardware processors an occurrence of a triggering event.

6. The computer-implemented method of claim 1, wherein detecting modification of the field corresponds to determining via the one or more hardware processors an occurrence of a triggering event that is associated with execution, via the one or more hardware processors, of the procedurally defined workflow within a locally executed application.

7. The computer-implemented method of claim 6, further comprising (a) identifying a plurality of field addresses associated with the plurality of database fields prior to the determining and (b) executing a routine that is configured to write the plurality of values to a set of entity-data fields based on the identifying.

8. One or more non-transitory media having instructions that, when executed by one or more hardware processors, cause the one or more hardware processors to perform a plurality of operations, the operations comprising:

detecting modification of a field, of a plurality of database fields, for a database record via a set of procedurally executed code that is monitoring operations associated with a database maintaining the database record;

responsive to detecting the modification of the field:

extracting, via the set of procedurally executed code, a plurality of values stored in the plurality of database fields for the database record, wherein the plurality of values comprises an identifier;

determining an electronic entity based on one or both of the identifier extracted via the set of procedurally executed code and the plurality of values, the electronic entity comprising a plurality of entity-data fields;

updating the plurality of entity-data fields, of the electronic entity, based on the plurality of values extracted from the plurality of database fields by the set of procedurally executed code;

subsequent to updating the plurality of entity-data fields of the electronic entity, computing a first class of the electronic entity based on inferences of a reasoner, drawn from a knowledge-based library based at least in part on the plurality of entity-data fields of the electronic entity;

returning classification data, corresponding to the first class, for the electronic entity as input to a procedurally defined workflow; and executing a workflow action within the procedurally defined workflow based on the classification data.

9. The one or more non-transitory media of claim 8, wherein the operations further comprise: determining, by the reasoner, a medical diagnostic class, wherein the electronic entity is determined to belong to the medical diagnostic class based on logical consequences of a plurality of health data values associated with the electronic entity, and wherein the classification data comprises the medical diagnostic class.

10. The one or more non-transitory media of claim 8, wherein the classification data indicates a diagnosis of the electronic entity and is returned as input to the procedurally defined workflow.

11. The one or more non-transitory media of claim 10, wherein the operations further comprise executing the workflow action within the procedurally defined workflow using the classification data.

12. The one or more non-transitory media of claim 8, wherein detecting modification of the field corresponds to determining via the one or more hardware processors an occurrence of a triggering event.

13. The one or more non-transitory media of claim 8, wherein detecting modification of the field corresponds to determining via the one or more hardware processors an occurrence of a triggering event that is associated with execution, via the one or more hardware processors, of the procedurally defined workflow within a locally executed application.

14. The one or more non-transitory media of claim 13, wherein the operations further comprise (a) identifying a plurality of field addresses associated with the plurality of database fields prior to the determining and (b) executing a routine that is configured to write the plurality of values to a set of entity-data fields based on the identifying.

15. A system having one or more hardware processors configured to perform a plurality of operations, the operations comprising:

detecting modification of a field, of a plurality of database fields, for a database record via a set of procedurally executed code that is monitoring operations associated with a database maintaining the database record;

responsive to detecting the modification of the field:

extracting, via the set of procedurally executed code, a plurality of values stored in the plurality of database fields for the database record, wherein the plurality of values comprises an identifier;

determining an electronic entity based on one or both of the identifier extracted via the set of procedurally executed code and the plurality of values, the electronic entity comprising a plurality of entity-data fields;

updating the plurality of entity-data fields, of the electronic entity, based on the plurality of values extracted from the plurality of database fields by the set of procedurally executed code;

subsequent to updating the plurality of entity-data fields of the electronic entity, computing a first class of the electronic entity based on inferences of a reasoner, drawn from a knowledge-based library based at least in part on the plurality of entity-data fields of the electronic entity;

returning classification data, corresponding to the first class, for the electronic entity as input to a procedurally defined workflow; and executing a workflow action within the procedurally defined workflow based on the classification data.

16. The system of claim 15, wherein the operations further comprise: determining, by the reasoner, a medical diagnostic class, wherein the electronic entity is determined to belong to the medical diagnostic class based on logical consequences of a plurality of health data values associated with the electronic entity, and wherein the classification data comprises the medical diagnostic class.

17. The system of claim 15, wherein the classification data indicates a diagnosis of the electronic entity and is returned as input to the procedurally defined workflow.

18. The system of claim 17, wherein the operations further comprise executing the workflow action within the procedurally defined workflow using the classification data.

19. The system of claim 15, wherein detecting modification of the field corresponds to determining via the one or more hardware processors an occurrence of a triggering event.

20. The system of claim 15, wherein the operations further comprise (a) identifying a plurality of field addresses associated with the plurality of database fields prior to the determining and (b) executing a routine that is configured to write the plurality of values to a set of entity-data fields based on the identifying.

* * * * *